United States Patent [19]

Telang

[11] Patent Number: 4,516,973

[45] Date of Patent: May 14, 1985

[54] ONE-PIECE DISPOSABLE COLLECTION BAG HAVING A RIGID COVER FOR A SUCTION CANISTER UNIT

[75] Inventor: Anil Telang, Elizabeth, N.J.

[73] Assignee: Becton, Dickinson and Company, Paramus, N.J.

[21] Appl. No.: 474,770

[22] Filed: Mar. 14, 1983

[51] Int. Cl.³ .............................................. A61M 1/00
[52] U.S. Cl. ..................................................... 604/319
[58] Field of Search .................. 604/317–320, 604/403, 408; 128/202.29, 205.15; 215/12 R, 11 E; 220/460, 461, 326, 403, 404, 408–410; 137/205

[56] References Cited

U.S. PATENT DOCUMENTS

| | | | |
|---|---|---|---|
| 1,948,263 | 2/1934 | Green | 220/326 |
| 3,768,478 | 10/1973 | Fertik et al. | 128/276 |
| 4,111,204 | 9/1978 | Hessel | 128/276 |
| 4,275,732 | 6/1981 | Gereg | 128/276 |
| 4,379,455 | 4/1983 | Deaton | 604/320 |
| 4,397,643 | 8/1983 | Rygiel | 604/317 |

Primary Examiner—C. Fred Rosenbaum
Assistant Examiner—J. L. Kruter
Attorney, Agent, or Firm—Richard J. Rodrick

[57] ABSTRACT

A suction canister assembly comprises a receptacle having an open end. A one-piece, integrally formed enclosed liquid collection container is removably positioned and supported in the receptacle. A port is available for providing suction to the interior of the container, and an opening in the container is available for drawing liquid into the container under suction conditions.

A liquid collection container for a suction canister assembly comprises a one-piece sealed, integrally formed flexible bag. The bag has a top portion relatively more rigid than a side portion and has an opening through the top portion and an opening through the side portion.

19 Claims, 4 Drawing Figures

ONE-PIECE DISPOSABLE COLLECTION BAG HAVING A RIGID COVER FOR A SUCTION CANISTER UNIT

BACKGROUND OF THE INVENTION

1. Field of the Invention

The present invention relates to the field of suction canisters, and more particularly, concerns a suction canister assembly used for withdrawing and collecting body fluids from a patient during surgical or respiratory procedures utilizing a one-piece disposable collection bag, and also concerns a disposable liquid collection container for a suction canister assembly.

2. Description of the Prior Art

Suction canisters are employed in the hospital environment, and particularly during surgical or respiratory procedures, to drain body liquids from a patient. In general, suction canisters employ a collection system and a vacuum source, such as a pump, to facilitate this drainage procedure. The canister generally includes a flexible tubing connected to the vacuum source so that vacuum can be applied to the interior of the canister. Another flexible tube extends from the canister to the source of body liquids in the patient. Once the vacuum is applied, a negative pressure gradient is communicated through the interior of the suction canister so that the body liquids are drawn into the canister.

Many canisters today rely upon a flexible bag or liner which is insertable into the canister immediately prior to use during surgical or respiratory drainage procedures. Liquids from the patient are collected into the flexible bag which is then removed from the canister upon being filled, and then the bag and contents are discarded. The canister receptacle itself may be retained and reused. In employing the flexible bag technique for suction canisters, the manufacturers of these devices have generally provided the bag as a packaged unit with a cover for the suction canister. To use the flexible bag, the operator would attach the cover to the canister so that the bag depends into the interior of the canister. A snap-tight fit retains the cover, with bag sealed thereto, on the canister during use. When the drainage procedure has been completed, the operator removes the cover along with the attached bag and contents therein. Representative suction canisters having a removable cover and flexible bag or liner attached thereto are described in U.S. Pat. Nos. 4,275,732; 4,111,204; 3,768,478; 3,719,197 and 3,680,560.

In order to simplify the suction drainage procedures utilizing suction canisters, it is desirable to eliminate the standard cover for suction canister assemblies. It is appreciated that placement of the cover on the canister, and its removal from the canister when the drainage procedure is completed, represent steps which take time and expense. Elimination of the canister cover also reduces the amount of material to be disposed of when the drainage procedure is completed. Manufacturing savings by eliminating the canister cover can be achieved as well. It is to these improvements in suction canister assemblies that the present invention is directed.

SUMMARY OF THE INVENTION

The suction canister assembly of the present invention comprises a receptacle having an open end. A one-piece, integrally formed enclosed liquid collection container is removably positioned and supported in the receptacle. Means provides suction to the interior of the container and draws liquid into the container under suction conditions.

In a preferred embodiment of this aspect of the invention, the receptacle is cylindrically shaped and a one-piece bag is removably positioned in the receptacle. This bag preferably has flexible sidewalls and a top wall relatively more rigid than the sidewalls extending across the open end of the receptacle. Means for sealing the cover across the open end of the receptacle in a vacuum-tight relationship is provided. An opening is provided in the receptacle, so that when connected to a source of vacuum, suction can be applied to the interior of the receptacle. The bag has an aperture in the sidewall to facilitate the inside fluid to communicate with the suction on the outside, when vacuum is applied through the suction opening on the receptacle. A liquid inlet port is in the top wall of the bag and is adapted to communicate with a source of liquid exterior to the canister assembly so that liquid is passable therethrough to enter the bag under suction conditions provided through the suction opening and the aperture.

In another aspect of the present invention, a liquid collection container comprises a one-piece sealed, integrally formed flexible bag having a top portion relatively more rigid than a side portion. The bag has an opening through the top portion and another opening through the side portion.

In a preferred embodiment of this other aspect of the invention, the container comprises a one-piece sealed bag having flexible sidewalls and a top wall relatively more rigid than the sidewalls. An aperture is in a sidewall adapted to serve as a vacuum inlet to the interior of the bag. A liquid inlet port in the top wall of the bag is adapted to communicate with a source of liquid so that liquid is passable therethrough to enter the bag under suction conditions provided through the aperture.

In accordance with the principles of the present invention, the one-piece construction of a disposable collection bag advantageously eliminates the need for a canister cover as utilized in previously known canister assemblies. The one-piece disposable collection bag of the present invention allows greater simplicity in assembling the canister assembly and in removing the bag and contents when the drainage procedure has been completed. Moreover, elimination of the cover provides savings in the cost of material and labor associated with the canister assembly. In addition, when the drainage procedure has been completed, there is less plastic material to dispose of, thereby providing a benefit to the environment. Inasmuch as the preferred flexible bag of the present invention may be collapsed prior to use, it facilitates its handling and shipping, particularly before use. In addition, the preferred flexible bag of the present invention lends itself to convenient manufacturing processes, such as a blow molding process, which can contribute to manufacturing savings.

DETAILED DESCRIPTION

Figure 1:
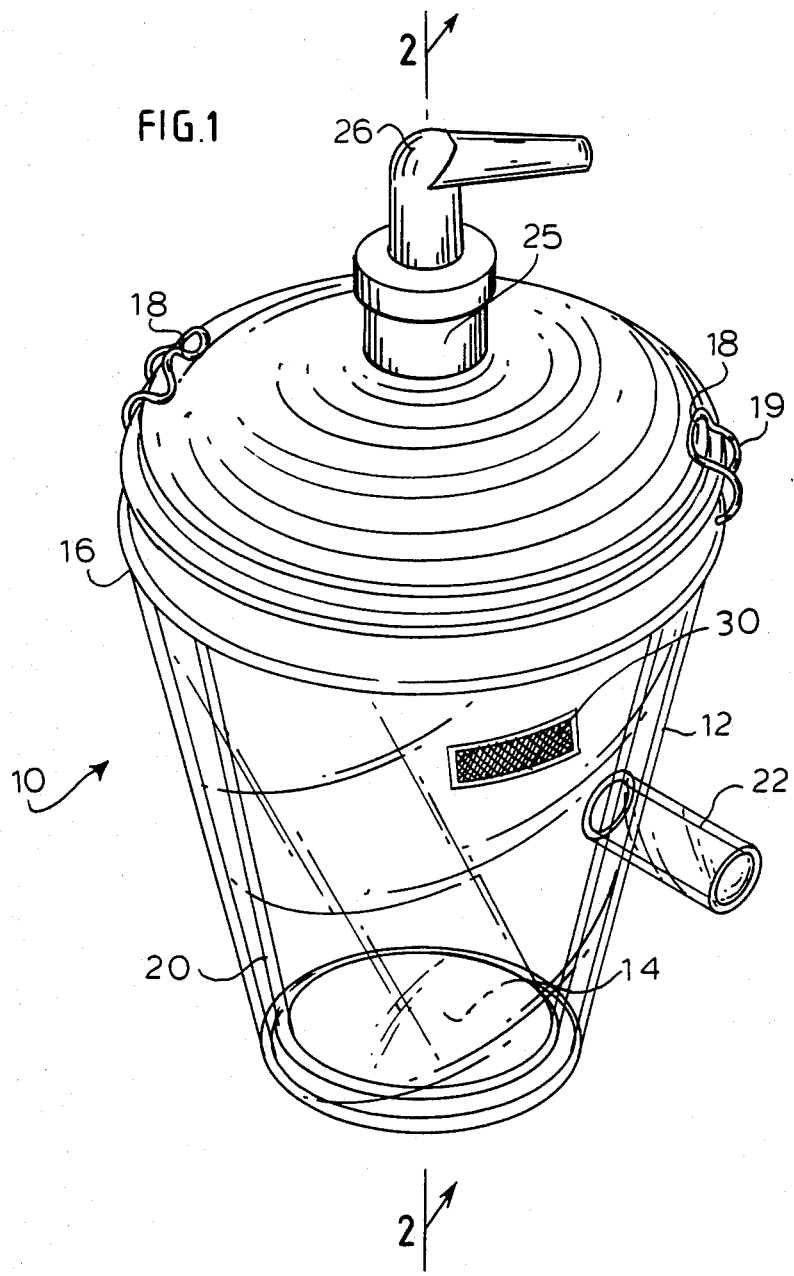
FIG. 1 is a perspective view of the preferred embodiment of the suction canister assembly of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
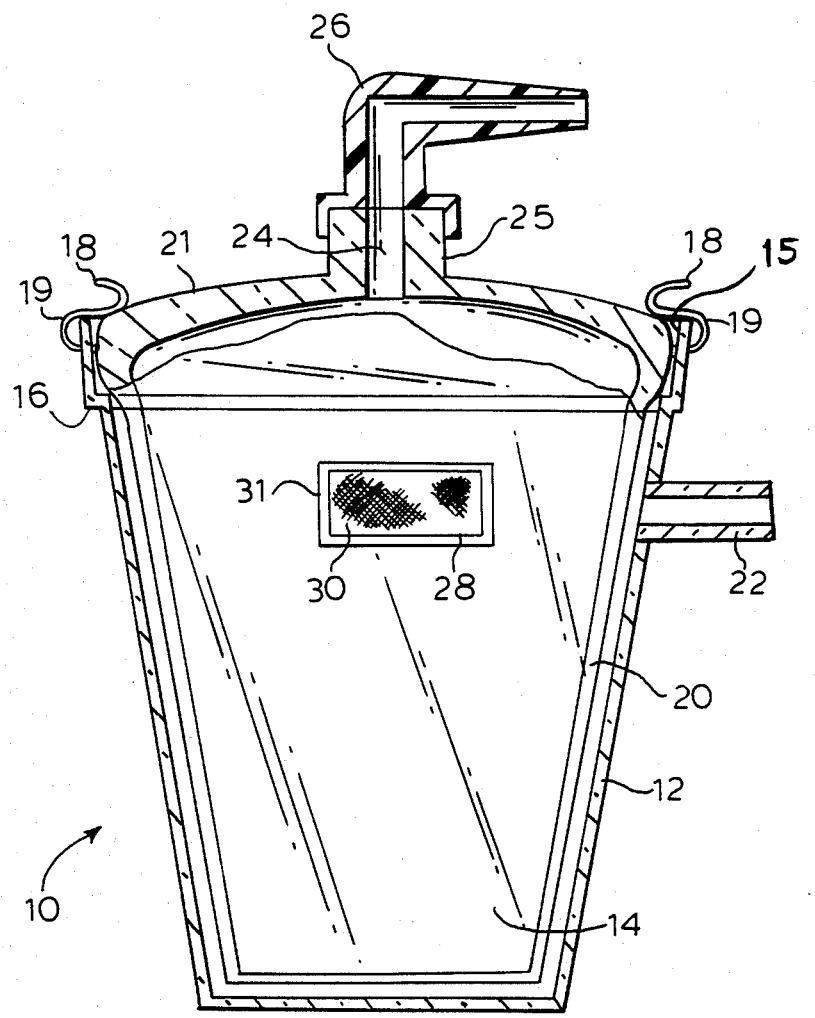
FIG. 2 is a cross-sectional view of the assembly of FIG. 1 taken along line 2—2.
Figure 3:
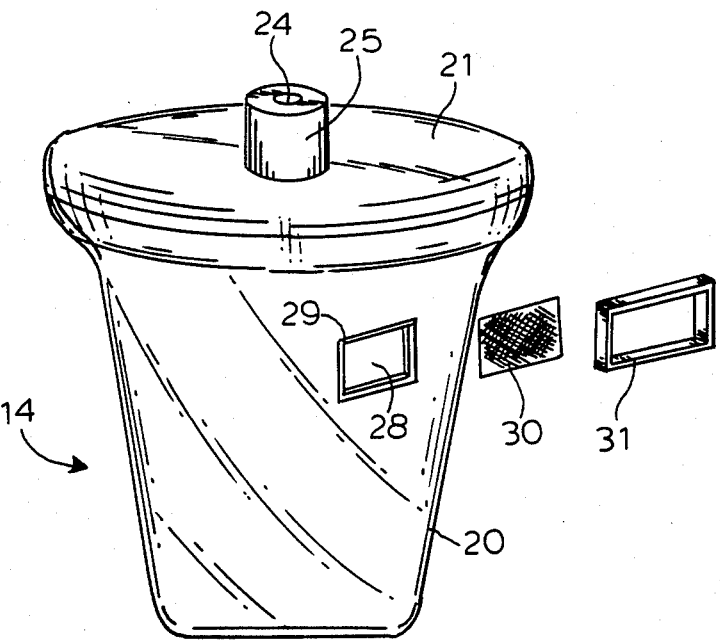
FIG. 3 is a perspective view, in partially exploded section, illustrating the preferred structure of the flexible bag for the assembly of FIG. 1.

Referring to the drawings, and FIGS. 1-3 in particular, there is illustrated a suction canister assembly 10. Suction canister assembly 10 is preferably composed of two major elements: a receptacle 12 and an enclosed liquid collection container 14, preferably in the form of a one-piece sealed, flexible plastic bag. The receptacle is preferably made of clear, rigid plastic material, and is cup-shaped with an open end 15. An annular shoulder 16, with a diameter slightly larger than the diameter of the cylindrical receptacle, extends around open end 15. An actuatable clamp 18 is connected to annular shoulder 16 by a pin 19 or the like. Clamp 18 is positioned on the annular shoulder so that it is movable to allow the flexible bag to be placed into the receptacle whereupon the clamp is positioned to make contact with the top wall of the flexible bag to tightly secure the bag in the receptacle. Typical suction canisters may hold a volume of one thousand to fifteen hundred cubic centimeters of fluid. However, these volumes may vary according to choice and the intended use of the suction canister.

Flexible bag 14 is preferably shaped so that when expanded it conforms to the interior walls of the receptacle. To this end flexible bag 14 includes flexible sidewalls 20, preferably continuous with each other to form a cylindrical cross-section. In addition, bag 14 includes a top wall 21 relatively more rigid than the sidewalls. Top wall 21 preferably has a circular cross-section so that it may extend across open end 15 of the receptacle. In the most desirable form of the present invention, both top wall 21 and sidewalls 20 are integrally formed so that bag 14 is a completely sealed, enclosed liquid collection container. The top wall of this bag is of sufficiently rigid construction to be substantially self-supporting under its own weight and also the weight of the inlet port thereon, as described hereafter. To achieve this relatively greater rigidity in the top wall, it is possible to fabricate bag 14 so that top wall 21 has a thickness ranging between 0.050 and 0.125 inches and approximately ten times the thickness of the sidewalls. Such differences in thickness in the flexible bag may be accomplished by a blow molding process.

Receptacle 12 includes a suction opening 22 through a side portion thereof. This suction opening is preferably in the form of a connector having an internally open passageway. This connector is adapted to be connected to a tube or hose for communication with a source of vacuum applied to the interior side of the receptacle. It is preferred that suction opening 22 be positioned through the receptacle at a location below annular shoulder 16 so that the vacuum applied through the suction opening is in direct communication with the sidewalls of flexible bag 14.

Top wall 21 includes a liquid inlet port 24 therethrough. A post 25 preferably protrudes from the upper surface of top wall 21 with the liquid inlet port being substantially centrally located therethrough. Removably connected to post 25 is a connector 26 which is in fluid communication with the liquid inlet port. Connector 26 is readily attachable to a tube or hose and is adapted to communicate with a source of liquid exterior to the canister assembly so that liquid is passable therethrough to enter the bag under suction conditions. The source of liquid in many instances will be liquid to be drained from a patient during a surgical procedure.

As more clearly seen in FIG. 3, sidewalls 20 include an aperture 28. When the aperture is formed in the flexible bag, a slightly protruding rim 29 may be formed around the periphery of the aperture. It is understood that the rim may also be constructed as a separate piece attached to the sidewall in the area around the periphery of the aperture. Covering the aperture is a gas-pervious liquid-impervious material 30 which serves to prevent liquid from escaping the bag through the aperture while allowing gases to pass therethrough particularly during suction conditions. A preferred gas-pervious, liquid-impervious material is a thin laminated membrane made of a composite polytetrafluoroethylene and a nonwoven polypropylene, presently commercially available from W. L. Gore and Associates of Elkton, Md. A snap-on cap 31 is preferably utilized to secure membrane 30 over aperture 28, with the snap-on cap mating in a tight-fight relationship over rim 29 on the flexible bag. It is understood, of course, that other techniques for securing the gas-pervious, liquid-impervious material to the flexible bag may be employed. It is also understood that other materials or devices may be used instead of the gas-pervious, liquid-impervious material, such as a one-way valve associated with the aperture to allow gas to pass therethrough, but to prevent liquid from escaping the bag through the aperture. The one-way valve element should be sufficient to terminate suction through the aperture when liquid rises in the bag to a predetermined level.

Figure 4:
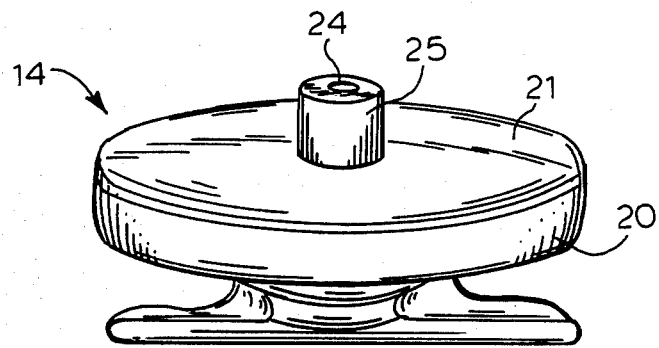
FIG. 4 is a perspective view of the flexible bag of FIG. 3 shown in a relatively flattened, collapsed condition prior to use.

Turning now to FIG. 4, it can be seen that sidewalls 20 of the bag 14 are sufficiently flexible to fold or collapse prior to use. Accordingly, the bag is placed in a relatively flattened condition during storage, shipment and handling prior to use. This feature clearly saves space before the bag is used in a suction canister.

In its preferred embodiment, bag 14 is a one-piece, sealed, integrally formed flexible plastic bag. The material of choice for the bag is polyethylene, although other materials may desirably be used.

When bag 14 is ready to be used in a suction canister, it is positioned in the receptacle as illustrated in FIGS. 1 and 2. Top wall 21 extends across open end 15 of the receptacle so that the top wall rests against and is supported by annular shoulder 16. Clamp 18 is moved into contact with top wall 21 thereby providing a vacuum-tight seal between bag and receptacle. The bag is thus supported in the canister so that it is prevented from collapsing and interfering with suction when suction is applied to the interior of the receptacle. A vacuum line is connected to suction opening 22 so that a suction force can be delivered to the interior of the receptacle. A tube or hose is connected to connector 26, the opposite end of which is placed in a source of liquid such as body fluids of a patient. When vacuum is applied, the suction enters the interior of the receptacle and is applied to the interior of bag 14 through the gas-pervious characteristics of material 30 and aperture 28. As a result, suction forces are applied through liquid inlet port 24 and connector 26 to draw liquid from the patient into the interior of the flexible bag. Liquid fills the bag until it rises to the level of aperture 28 and gas-pervious, liquid-impervious material 30. when the aperture is completely covered by liquid inside the bag, suction to the interior of the bag will be terminated so that the liquid will not over-fill the bag. The level of liquid to enter the bag can be predetermined by choosing the position of the aperture on the sidewalls of the bag. It should also be noted that the preferred rectangular shape of aperture 28 will allow a slow termination of the suction to the interior of the bag thereby providing some warning that the liquid level is approaching maximum.

When the bag has the desired amount of liquid therein, the vacuum to suction opening 22 is terminated. Clamp 18 is then disconnected from the top wall of the flexible bag, whereupon the liquid-filled bag is removed from the receptacle. The bag with contents is disposable, whereas the receptacle may be retained for further use.

Thus, the instant invention provides a suction canister assembly which includes a disposable flexible bag or liner and which eliminates the need to have a cover for the receptacle which is now utilized in the present suction canister assemblies.

What is claimed is:

1. A suction canister assembly comprising:
  a cup-shaped receptacle having an open end;
  a bag removably positioned and sealed in said receptacle, said bag having flexible sidewalls and a top wall relatively more rigid than said sidewalls extending across the open end of said receptacle said sidewalls and said top wall being integrally formed of one piece of the same material;
  means for sealing said top wall across said end in a vacuum-tight relationship whereby said top wall serves as an exterior cover for the canister assembly;
  said receptacle having a suction opening adapted to communicate with a source of vacuum applied to the exterior side of said suction opening;
  said bag having an aperture in a sidewall thereof adapted to be in fluid communication with said suction opening when suction is applied to said suction opening; and
  said bag having a liquid inlet port in the top wall thereof adapted to communicate with a source of liquid exterior to said canister assembly so that liquid is passable therethrough to enter said bag under suction conditions provided through said suction opening and said aperture.

2. The assembly of claim 1 wherein the sidewalls of said bag are continuous and generally conform to the shape of the interior of said receptacle.

3. The assembly of claim 1 wherein the top wall is sufficiently rigid to be substantially self-supporting under its own weight and the weight of the inlet port during use.

4. The assembly of claim 1 wherein said aperture includes a one-way valve associated therewith to allow gas to pass therethrough, but to prevent liquid from escaping the bag, through the aperture.

5. The assembly of claim 4 wherein said valve is adapted to terminate suction through said aperture when liquid rises in said bag to a predetermined level.

6. The assembly of claim 5 wherein said valve is a gas-pervious, liquid-impervious material covering said aperture.

7. The assembly of claim 1 wherein said means for sealing includes an annular shoulder around the open end of said receptacle and an actuatable clamp associated therewith for clamping the top wall of said bag onto said shoulder in a vacuum-tight seal.

8. The assembly of claim 1 wherein said bag is made of flexible plastic material.

9. A suction canister assembly comprising:
  a receptacle having an open end;
  a one-piece, flexible enclosed liquid collection container positioned in said receptacle, said container including an integrally formed top wall means serving as an exterior cover for the canister assembly;
  means for providing suction to the interior of said container and for drawing liquid in said container under said suction conditions; and
  means for supporting said flexible container in said receptacle to prevent the container from collapsing and interfering with suction when the suction is applied to the interior of said container.

10. The assembly of claim 9 wherein said means for supporting includes the top wall means of said container being sealed across the open end of said receptacle in a vacuum-tight relationship.

11. The assembly of claim 9 wherein said container is removably positioned in said receptacle.

12. A suction canister assembly comprising:
  a cylindrically shaped receptacle having an open end with an annular shoulder therearound;
  a sealed plastic bag shaped generally to conform to the interior walls of said receptacle positioned in said receptacle and having flexible sidewlls and a top wall means relatively more rigid than said sidewalls extending across the open end of said receptacle, said sidewalls and said top wall means being integrally formed of one piece of the same material, with said top wall means being sealed onto said shoulder in a vacuum-tight seal, said top wall means being sufficiently rigid to be substantially self-supporting whereby said top wall means serves as an exterior cover for the canister assembly;
  said receptacle having a suction opening adapted to communicate with a source of vacuum applied to the exterior side of said suction opening;
  said bag having an aperture in a sidewall thereof adapted to be in fluid communication with said suction opening when vacuum is applied to said suction opening;
  said bag having a liquid inlet port in the top wall thereof adapted to communicate with a source of liquid exterior to said canister assembly so that liquid is passable therethrough to enter said bag under suction conditions provided through said suction opening and said aperture; and
  a gas-pervious, liquid-impervious material covering said aperture to prevent liquid from escaping said bag through said aperture and to terminate suction through said aperture when liquid rises in said bag to completely cover said aperture.

13. A disposable liquid collection container for a suction canister assembly comprising:
  a sealed bag having flexible sidewalls and a top wall means relatively more rigid than said sidewalls forming an exterior cover, said sidewalls and said top wall means being integrally formed of one piece of the same material, said bag having an aperture in a sidewall thereof adapted to serve as a vacuum inlet to the interior of said bag, and having a liquid inlet port in the top wall means thereof adapted to communicate with a source of liquid so that liquid is passable therethrough to enter said bag under suction conditions provided through said aperture.

14. The container of claim 13 wherein the top wall is sufficently rigid to be substantially self-supporting under its own weight and the weight of the inlet port.

15. The container of claim 13 wherein the bag is substantially cylindrically shaped.

16. The container of claim 13 wherein said aperture includes a one-way valve associated therewith to allow gas to pass therethrough, but to prevent liquid from escaping the bag, through the aperture.

17. The container of claim 16 wherein said valve is a gas-pervious, liquid-impervious material covering said aperture.

18. The container of claim 13 wherein said sidewalls are collapsed so that said container is in a relatively flattened condition prior to use.

19. A disposable liquid collection container for a suction canister assembly comprising:
 a sealed plastic bag substantially cylindrically shaped having flexible sidewalls and a top wall means said sidewalls and said top wall means being integrally formed of the same material forming an exterior cover, said top wall means having a thickness ranging between 0.050 and 0.125 inches and ten times the thickness of the sidewalls, said bag having an aperture in a sidewall thereof adapted to serve as a vacuum inlet to the interior of said bag, and having a liquid inlet port in the top wall means thereof adapted to communicate with a source of liquid so that liquid is passable therethrough to enter said bag under suction conditions provided through said apertures; and
 a gas-previous, liquid-impervious material covering said aperture to prevent liquid from escaping the bag, but allow gas to pass therethrough.

* * * * *